United States Patent [19]

Monaghan

[11] Patent Number: 5,255,683
[45] Date of Patent: Oct. 26, 1993

[54] METHODS OF AND SYSTEMS FOR EXAMINING TISSUE PERFUSION USING ULTRASONIC CONTRAST AGENTS

[75] Inventor: Mark J. Monaghan, Croydon, England

[73] Assignee: Sound Science Limited Partnership

[21] Appl. No.: 816,640

[22] Filed: Dec. 30, 1991

[51] Int. Cl.$^5$ .............................................. A61B 8/06
[52] U.S. Cl. ................................................. 128/662.02
[58] Field of Search ......... 128/660.06, 661.07–661.10, 128/662.02

[56] References Cited

U.S. PATENT DOCUMENTS

| | | | |
|---|---|---|---|
| 3,640,271 | 2/1972 | Horton | 128/2.05 D |
| 4,122,713 | 10/1978 | Stasz et al. | 73/194 A |
| 4,140,022 | 2/1979 | Maslak | 73/626 |
| 4,265,251 | 5/1981 | Tickner | 128/660 |
| 4,276,885 | 7/1981 | Tickner et al. | 128/660 |
| 4,316,391 | 2/1982 | Tickner | 73/861.25 |
| 4,466,442 | 8/1984 | Hilmann et al. | 128/653 |
| 4,569,353 | 2/1986 | Ferrari | 128/660.06 |
| 4,572,203 | 2/1986 | Feinstein | 128/661 |
| 4,619,267 | 10/1986 | Launusel et al. | 128/660.06 |
| 4,718,433 | 1/1988 | Feinstein | 128/660 |
| 4,774,958 | 10/1988 | Feinstein | 128/660.01 |
| 4,803,994 | 2/1989 | Burke | 128/660.06 |
| 4,827,942 | 5/1989 | Lipschutz | 128/661.08 |
| 4,844,882 | 7/1989 | Widdler et al. | 424/9 |

OTHER PUBLICATIONS

Abstract entitled *Digital Acquisition and Processing of Myocardial Contrast Echocardiographic Signals* by Monaghan, et al. appearing in *Echocardiography* 1990 presented at the 7th International Congress on Echocardiography in Rome, Italy in Apr. 1990.

Abstract entitled *Detection of Myocardial Perfusion Using Intravenous Contrast Echocardiography*, presented to the British Cardiac Society and British Heart Journal, May, 1990.

Abstract entitled *Detection of Myocardial Contrast Using Backscatter Spectral Frequency Analysis* by Monaghan, et al. appearing in the European Heart Journal, Aug., 1990, p. 113.

Article entitled "Digital Echocardiographic Techniques in Myocardial Contrast Echocardiography" by Monaghan, et al. appearing in *Echocardiography* 1990, A. Dagianti and H. Feigenbaum, eds., pp. 235–244.

Paper entitled "Myocardial Contrast Echocardiography: Applications of Digital Ultrasound Data Acquisition and Processing" by Monaghan, et al. appearing in the *American Journal of Cardiac Imaging*, vol. 5, No. 3 (Sep., 1991: pp. 237-249).

Abstract entitled *Digital Radiofrequency Ultrasound Analysis of Myocardial Contrast Following I.V. Albunex Injection* by Monaghan, et al. appearing in the European Heart Journal, Aug. 1991.

Color Atlas of Real-Time Two-Dimensional Echocardiography, (R. Omoto, ed.), Shindan-To-Chiro Co., Ltd., Tokyo (1984) pp. 7–36.

Mark J. Monaghan, Practical Echocardiography and Doppler, John Wiley and Sons, (1990, reprinted Jul. 1991), chapters 1 and 11.

Harvey Feigenbaum, Echocardiography, Lea and Febiger, (1981), chapter 1.

Digital Techniques in Echocardiography, (Jay Roelandt, ed.), Martinus Najhoff Publishers, (1987), chapters 1–5.

Powsner, et al., *High Speed Interface for Myocardial Sonicated Echocontrast Studies*, appearing in SPIE, vol. 845, Visual Communications and Image Processing II, pp. 384–395 (1987).

(List continued on next page.)

*Primary Examiner*—Francis Jaworski
*Attorney, Agent, or Firm*—Marshall, O'Toole, Gerstein, Murray & Borun

[57] ABSTRACT

A system for and method of ultrasonically examining tissue using an ultrasound contrast enhancing agent involve detecting a frequency dependent characteristic of ultrasonic energy reflected from tissue at first and second time periods and utilizing the resulting data to obtain an indication of the presence in and the travel of the agent through the tissue.

48 Claims, 5 Drawing Sheets

OTHER PUBLICATIONS

Feinstein, *Myocardial Perfusion Imaging: Contrast Echocardiography Today and Tomorrow*, Journal of the American College of Cardiology, vol. 8, No. 1, Jul., 1986, pp. 251-253.

Feinstein, *New Developments in Ultrasonic Contrast Techniques: Transpulmonary Passage of Contrast Agents and Diagnostic Implications*, Echocardiography, vol. 6, No. 1, pp. 27-33, 1989, presented at CardioVision '88 Monaco, Jun. 16-18, 1988.

Feinstein, et al., *Safety and Efficacy of a New Transpulmonary Ultrasound Contrast Agent: Initial Multicenter Clinical Results*, Journal of the American College of Cardiology, vol. 16, No. 2, pp. 316-324, Aug., 1990.

*Cardiac Imaging-Principles and Practice*, Marcus et al. eds., W. B. Sanders Company, Philadelphia, 1990. Chapter 27, "Contrast Echocardiography", pp. 557-574 by Feinstein et al.

Sahn, *3rd Annual University of Chicago Symposium on Advances in Echocardiography*, Sound Practice, vol. 1, pp. 1-8.

Kern, *Microbubbles Show Promise for Enhancing Ultrasound Signal, Image, Other Applications*, Journal of the American Medical Association (JAMA), vol. 261, No. 11, pp. 1542, Mar. 17, 1989.

Newspaper article entitled "Ultrasound Enters New Frontiers" appearing at *The New York Times* dated Nov. 28, 1990.

Product brochure entitled "Albunex Ultrasound Contrast Agent" by Molecular Biosystems, Inc. of San Diego, Ca.

Press Release from Molecular Biosystems, Inc. entitled "Molecular Biosystem's Albunex TM Classified as a Device by FDA".

Sutro and Co., Inc., Basic Report dated Aug. 3, 1988.

Hayes and Griffith, Inc., Basic Report dated Apr. 29, 1987.

Kidder, Peabody Equity Research, Company Analysis dated Feb. 15, 1989.

Kidder, Peabody Equity Research, Company Comment dated Sep. 28, 1989.

Hayes and Griffith, Inc., Update dated Oct. 7, 1987.

Syllabus entitled "Advances in Echocardiography: Contrast Echocardiography, Perfusion Imaging, Transesophageal Echo", dated Oct. 4-5, 1991.

Pages 1-76 of the book by PNT Wells entitled "Physical Principles of Ultrasonic Diagnosis", Academic Press, London (1969).

Excerpt from *Science News*, vol. 140, No. 13, pp. 207, Sep. 28, 1991.

Newspaper article entitled "New Technique Locates Hidden Breast Cancer", appearing at pp. 1 and 18 of *The Chicago Sun Times* dated Dec. 3, 1991.

METHODS OF AND SYSTEMS FOR EXAMINING TISSUE PERFUSION USING ULTRASONIC CONTRAST AGENTS

TECHNICAL FIELD

The present invention relates generally to medical examination methods and systems, and more particularly to methods and systems, and more particularly to methods and systems for examining tissue using ultrasonic energy and ultrasound-specific contrast agents.

BACKGROUND ART

Ultrasonic techniques are commonly used in medical imaging systems to study the anatomy and function of organs and other tissue structures within the body. Such systems typically energize a transducer to transmit short pulses of ultrasound into the body. The backscattered ultrasonic energy reflected by acoustic interfaces within the body is converted by the transducer into an electrical signal. The amplitude of the signal at various points in time is detected and this information is utilized to construct a moving image representing a tomographic slice through parts of the body. Such systems are also capable of obtaining information about the direction and velocity of blood flow within the body utilizing Doppler techniques. Referring to FIG. 1, a curve 8 represents the frequency spectrum transmitted by the transducer. The Doppler effect resulting from ultrasound striking moving red blood cells manifests itself as a shifting of the entire frequency spectrum upwardly or downwardly without a significant change in overall spectrum shape, as illustrated by the curves 9a and 9b of FIG. 1. This shift is detected and, in Doppler color flow mapping systems, the imaging system causes different colors and intensities to be superimposed on the moving image based upon the detected shift so that an indication of direction and velocity of blood flow is obtained. A different type of system known as a spectral Doppler display system creates a graphical display of blood flow velocity and direction plotted against time.

More recently, ultrasound contrast agents have been developed to allow the study of perfusion or distribution of blood supply within body tissues. Such contrast agents are commonly made of small microbubbles or gas filled spheres. Such contrast agents are strong scatters of ultrasound. Hence, if they are injected or delivered into the blood supply of an organ or other tissue, their passage therethrough can be detected by examining the increase in backscattered ultrasonic intensity using standard ultrasound imaging equipment like that described above. Semi-quantitative assessment of degrees of perfusion may be obtained using additional equipment that can analyze the magnitude of increase in backscattered intensity. Also, various temporal parameters can be measured which relate to the number of blood cells and contrast microbubbles flowing through specific areas of tissues. Such systems have the disadvantage, however, in that a large number of contrast microbubbles must be delivered into the tissue to provide a sufficient change in backscattered intensity that can be reliably detected.

Recent improvements in the production of contrast agents has led to the development of microbubbles of an acceptably consistent size on the order of the size of red blood cells or smaller. Such microbubbles can travel through the lungs into the arteries following an intravenous injection and hence these contrast agents can reach organ tissues without the need to perform arterial catheterization. While the use of such contrast agents involves less risk and is less expensive and more convenient to use than agents that must be delivered via catheterization into an artery, it appears that the number of contrast microbubbles reaching organ tissues following intravenous injection is insufficient to permit reliable evaluation of tissues using changes in backscattered intensity. In addition, variable attenuation of the ultrasound signals by body tissues and the contrast agent in the space between the transducer and the tissues to be studied limits the use of methods reliant upon changes in backscatter intensity for evaluation of relative perfusion.

SUMMARY OF THE INVENTION

In accordance with one aspect of the present invention, a method of and system for ultrasonically examining tissue using an ultrasound contrast enhancing agent detects one or more changes in a frequency characteristic of the ultrasonic energy rather than changes in backscatter intensity.

More particularly, in accordance with this aspect of the present invention, a method of ultrasonically examining tissue using an ultrasound contrast enhancing agent includes the steps of insonating the tissue with ultrasonic energy during a first time period in the absence of a contrast agent in the tissue and during a second time period in the presence of a contrast agent in the tissue, detecting a frequency characteristic of ultrasonic energy during the first time period to obtain baseline frequency data and detecting the frequency characteristic of the ultrasonic energy reflected by the tissue during the second time period to obtain post-introduction frequency data. The baseline frequency data and the post-introduction frequency data are used to obtain an indication of presence of the agent in the tissue.

Preferably, the step of detecting the frequency characteristic during the first and second time periods comprises the step of detecting the amplitudes of first and second frequency components. Further in accordance with this aspect of the present invention, the first and second frequency amplitudes detected during the first time period are divided to derive a first ratio, the first and second frequency amplitudes detected during the second time period are divided to derive a second ratio and the first and second ratios are compared. A display is preferably operated in accordance with the comparison of the first and second ratios to obtain the indication of presence of the agent.

If desired, the display may be of the color type and image data representing an image of the tissue may be derived from the reflected ultrasonic energy. A color coder may develop color display data based on the comparison of the first and second ratios and the image data and the color display data may be combined and provided to the display.

Preferably, the step of detecting the frequency characteristic during the first and second time periods includes the step of providing a reflection signal developed by a transducer to first and second bandpass filters having center frequencies substantially equal to the first and second frequencies to obtain first and second filtered signals. The amplitudes of the first and second filtered signals are divided to obtain the above mentioned first and second ratios.

In accordance with alternative embodiments of the present invention, the first and second bandpass filters may be replaced by one or more frequency analyzers, which may process the reflection signal using a fast Fourier transformation algorithm or a Chirp-Z algorithm. Still further, the frequency analyzer may comprise a zero crossing detector or an autocorrelation frequency estimator.

In yet another alternative embodiment, a transducer may be operated to sequentially insonate the tissue with ultrasonic energy at first and second frequencies. The reflection signal developed by the transducer is then applied to first and second amplitude detectors that detect the first and second frequency amplitudes.

In each of the embodiments of the invention, the ultrasonic energy may be directed sequentially along scan lines and the frequency dependent characteristic of the ultrasonic energy during the first and second time periods is determined a plurality of times for each scan line.

In accordance with another aspect of the present invention, a system for detecting tissue perfusion using a contrast agent includes a transducer capable of directing ultrasonic energy at first and second different frequencies to tissue wherein the contrast agent has a resonant frequency in the tissue and the first frequency is substantially equal to the resonant frequency. The transducer is also capable of developing a baseline reflection signal and a post introduction reflection signal representative of ultrasonic energy reflected by the tissue prior to and after introduction of the contrast agent into the tissue, respectively. Means are coupled to the transducer for detecting a frequency characteristic of the baseline reflection signal and the post-introduction reflection signal and means are also provided for developing an indication of tissue perfusion therefrom.

In accordance with yet another aspect of the present invention, a system for ultrasonically examining blood flow through at least a part of a living body using a contrast agent injectable into the flow of blood through the part includes means for insonating the part with ultrasonic energy at first and second frequencies during a first time period when the contrast agent is present in the part and during a second time period when contrast agent is not in the part and means for detecting amplitudes of first and second frequency components of the ultrasonic energy reflected from the part during the first and second time periods. Means are coupled to the detecting means for comparing the amplitudes detected during the first time period with the amplitudes detected during the second time period. Means are coupled to the comparing means for operating a display in accordance with the comparison to obtain an indication of blood flow.

DESCRIPTION OF THE PREFERRED EMBODIMENTS

Figure 1:
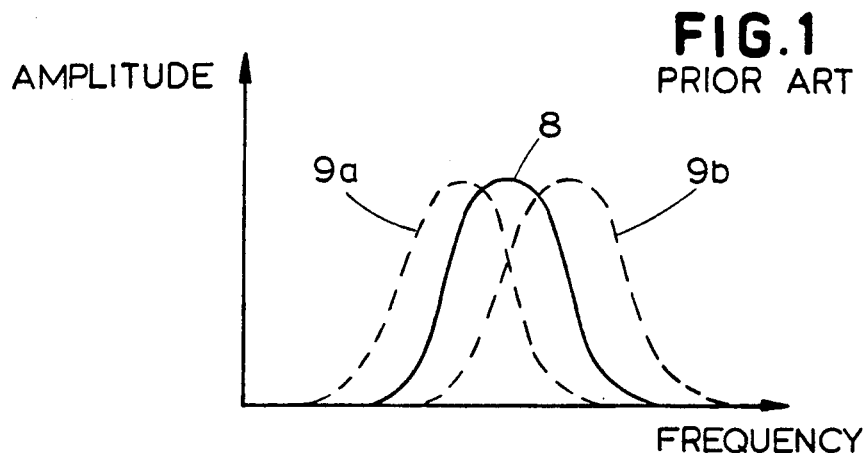
FIG. 1 comprises a series of curves illustrating transmitted and reflected frequency spectra in a conventional system utilizing Doppler techniques.
Figure 2:
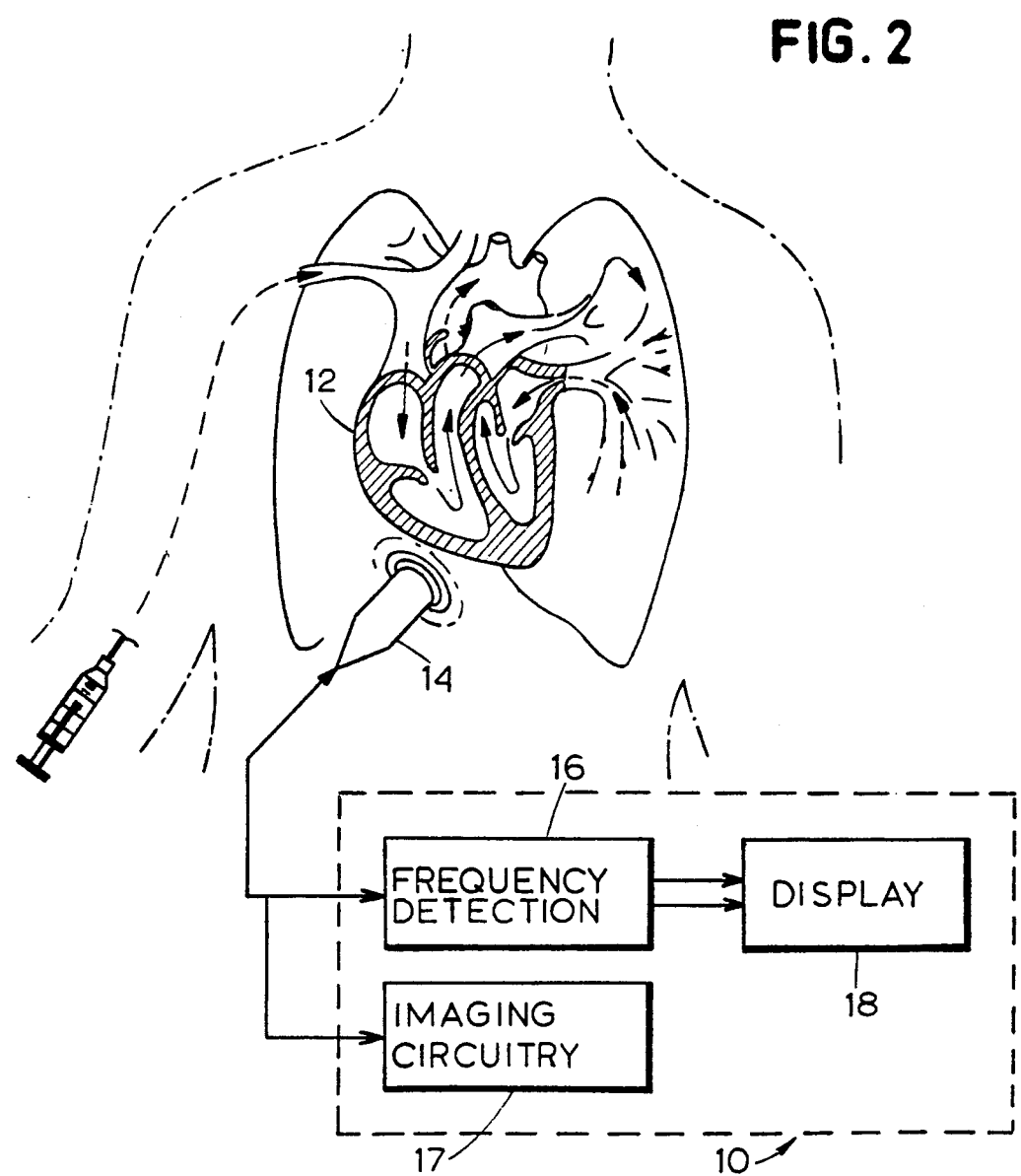
FIG. 2 comprises a block diagram of a system according to the present invention during imaging of human myocardium.

Referring now to FIG. 2, there is illustrated a system 10 for ultrasonically examining tissue, such as human myocardium (or heart) 12. It should be noted that the system 10 is also useful in the examination of other tissues, such as other organs or muscle. The system 10 includes a transducer 14, which may comprise, for example, a piezoelectric element that may be driven over a band or spectrum of frequencies with a center frequency of, for example, 2.5 megahertz. This center frequency and the shape of the spectrum may be varied to obtain optimum imaging as needed. The transducer is in turn coupled to a frequency detection circuit 16 that detects one or more parameters of the ultrasonic energy reflected by the body tissues and imaging circuitry 17. A display 18, which may be of the color type, displays an image of the tissue being examined.

As noted previously, the system 10 according to the present invention is particularly useful in the examination of blood flow or perfusion through human tissues using a contrast enhancing agent. While any suitable contrast agent may be used, the contrast agent preferably comprises ALBUNEX® (a registered trademark of Molecular Biosystems, Inc. of San Diego, California). This contrast agent includes sonicated microbubbles or microspheres formed of denatured proteins or derivatives thereof obtained from an aqueous protein solution of human serum albumin. The contrast agent may be introduced into the tissue via a vein or artery, inasmuch as the microbubbles have a size which permits their passage through the capillaries of the lungs and into the myocardium 12.

It has been found that contrast microbubbles have a resonant in-vivo frequency. This resonant frequency depends upon a number of factors including the size of the microbubble or microsphere and the surrounding medium, pressure and temperature. The present invention utilizes the theory that because microbubbles have a resonant frequency, they should not be perfect, uniform scatterers of all ultrasound frequencies. The amount of ultrasound energy backscattered depends upon the specific frequency of the ultrasound. This effect permits detection of perfusion by analyzing changes in the backscattered frequency spectrum from diagnostic ultrasound pulses when microbubbles are delivered into the tissue. This change in the frequency spectrum of backscattered ultrasound pulses is greater in statistical significance than changes in the amplitude (i.e. intensity) of the backscattered signal and provides the basis for more sensitive detection of ultrasonic contrast agents.

Depending on the microbubble physical parameters and the center frequency of the ultrasound transducer, changes in the backscattered frequency spectrum following introduction of microbubbles into an area of tissue being insonated (examined) by an ultrasound transducer and attached imaging equipment are likely to include a large shift in the overall mean frequency, attenuation of selected frequencies and a change in the useful bandwidth of the backscattered frequency spectrum. The precise nature of all these changes depends upon the concentration, size and medium of the microbubbles, the characteristics of the transducer including bandwidth, center frequency and frequency sensitivity and, perhaps, the type of body tissue being examined (and its own backscatter characteristics). Nevertheless, in most circumstances, these changes are large enough to be easily detected. If the microbubble invivo characteristics are such that its resonant frequency is low when compared to the transducer center frequency, then attenuation of the lower frequency components of the backscattered signal will result a net upward shift in the mean frequency of the backscattered ultrasound signal. Conversely, if the resonant frequency of the microbubbles is higher than the transducer center frequency, then attenuation of the higher frequency components will result in a downward shift in the mean frequency. Therefore, this effect may be detected using known commercially available diagnostic ultrasound imaging systems together with additional components to provide an alternative method of evaluating contrast microbubbles within body tissue.

Feinstein U.S. Pat. Nos. 4,572,203, 4,718,433 and 4,774,958 disclose the above mentioned contrast enhancing agents and systems utilizing such agents and are expressly incorporated by reference herein.

Figure 3:
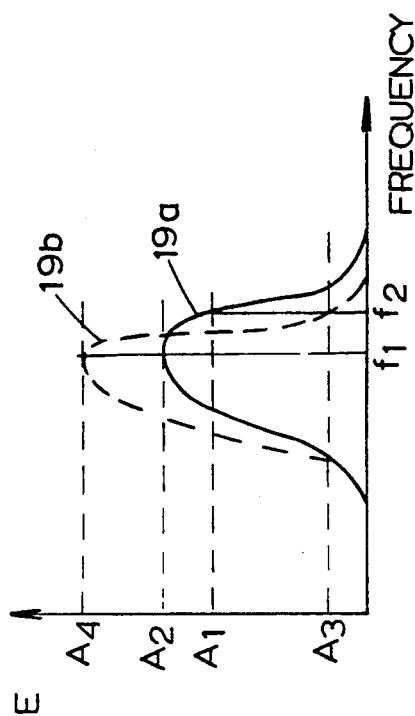
FIG. 3 comprises a pair of curves illustrating exemplary reflected baseline and post-introduction frequency spectra detected by the system of the present invention.

According to one aspect of the present invention, the tissue undergoing examination is insonated a first time in the absence of a contrast agent therein and reflected ultrasonic energy is detected and converted by the transducer 14 into a baseline reflection signal, which may comprise a voltage waveform. Referring also to FIG. 3, this baseline signal may have a frequency spectrum represented by the curve 19a. A frequency characteristic of the baseline reflection signal is detected by the detection circuit 16 and is stored in a memory (described hereinafter). The tissue undergoing examination is also insonated when a contrast agent is present therein (either before or after the baseline detection), and the reflected ultrasonic energy is received and converted by the transducer 14 into a post-introduction reflection signal. Again, this signal may be a voltage waveform. As seen in FIG. 3, the presence of the contrast agent may change the shape of the reflected frequency spectrum to the curve 19b, for example. A frequency characteristic of the post-introduction reflection signal is detected by the detection circuit 16, compared against the frequency characteristic stored in the memory and the display 18 is operated in accordance with the comparison to provide an indication of perfusion or blood flow.

Figure 4:
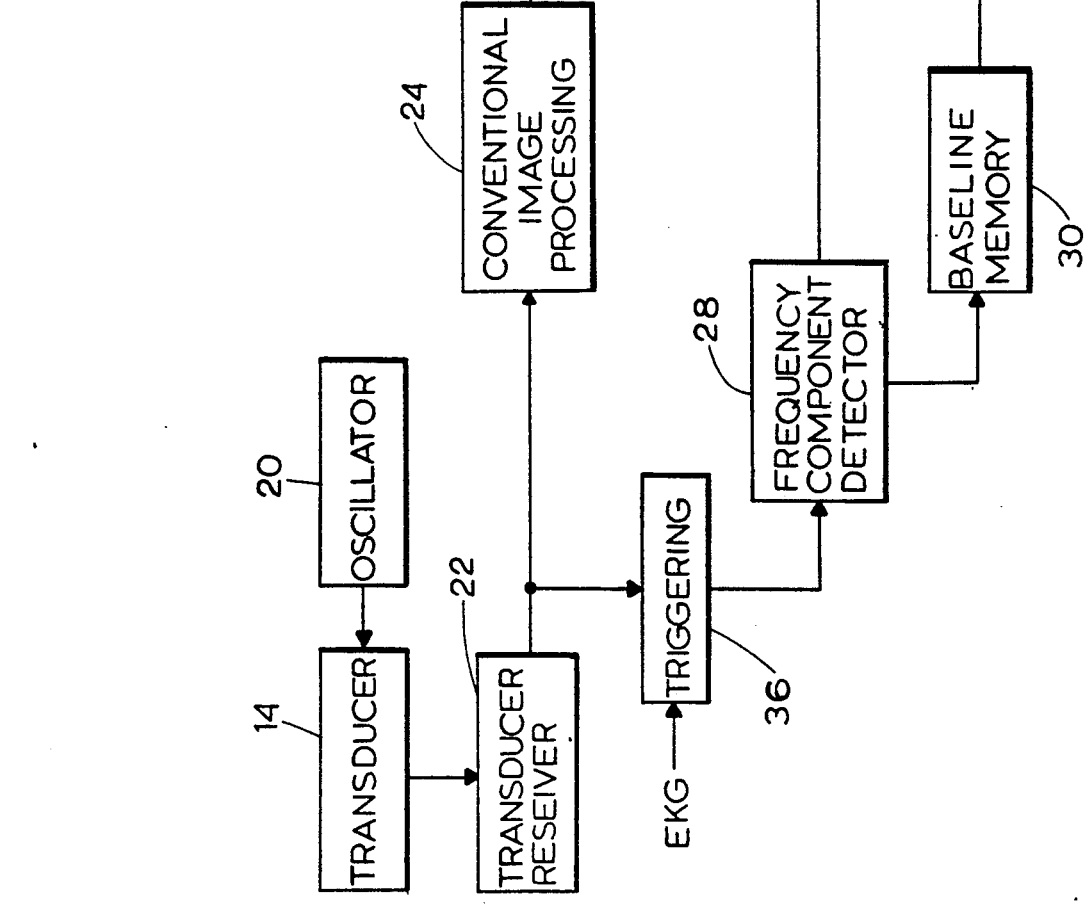
FIGS. 4-7 are block diagrams of systems comprising alternative embodiments of the present invention.

FIG. 4 illustrates a first embodiment of the present invention in greater detail. The transducer 14 is periodically excited by an oscillator 20 to sequentially provide ultrasonic energy over a first or incident frequency spectrum down a series of scan lines. The ultrasonic energy reflected by the tissues being examined is converted by the transducer 14 into a reflection signal, which is amplified to a proper signal level by a transducer receiver circuit 22. The reflection signal has a second or reflected frequency spectrum. As is conventional, the receiver circuit 22 may receive a blanking signal during transmission of ultrasonic energy by the transducer 14 until transmission of the energy for that scan line is complete and once a suitable ring down period has expired. The blanking signal is then removed, allowing the receiver 22 to receive the reflected signal from the transducer 14. A conventional image processing circuit 24 samples the reflection signal at spaced points thereof and integrates the resulting information with data obtained from other scan lines to obtain video display data which is provided to a combiner 26 and the display 18. This data typically results in a grey scale, real-time image of the tissue on the display 18.

The reflection signal from the receiver circuit 22 is also provided to a frequency detector in the form of a frequency analyzer 28 that detects one or more frequency characteristics of the reflection signal. In one embodiment of the present invention, the resonant frequency of the microbubbles in the tissue undergoing examination is determined and the transducer 14 is excited to produce a band of frequencies that includes the microbubble in-vivo resonant frequency. Preferably, although not necessarily, the center frequency of the transducer is not coincident with the microbubble in-vivo resonant frequency, but is spaced therefrom in the frequency spectrum. Also, in actuality, since the microbubbles are not all the same size and thus have slightly different resonant frequencies, a frequency within the range of resonant frequencies is assumed to be the in-vivo resonant frequency. The frequency component detector 28 analyzes the backscattered frequency spectrum at multiple points over each scan line in the imaging plane in real time using a Fast Fourier transformation algorithm or a Chirp-Z algorithm. During analysis of the baseline reflection signal, the magnitudes or amplitudes of first and second frequency components in the voltage signal developed by the transducer are detected. Preferably, although not necessarily, the first frequency is substantially equal to the microbubble in-vivo resonant frequency and the second frequency is at a selected frequency within the response band of the transducer but removed or spaced from the resonant frequency. In the preferred embodiment, the second frequency is substantially coincident with the transducer center frequency. These magnitudes are stored as data in a baseline memory 30. These data are compared against data representing the voltage magnitudes or amplitudes of these frequency components in the post-introduction reflection signal by a comparator 32. The result of the comparison is provided to a color coder 34, which provides further display data or information to the combiner 26 and the display 18. The color coder may simply be a lookup table that converts the comparator output into color display information that is combined by the combiner 26 with the video display data developed by the image processing circuit 24. The display 18 thus displays a grey scale image of the tissue with color superimposed thereon representing the travel of contrast agent through blood vessels therein. The resulting display image may be static (or frozen) or real-time. Alternatively, a combination of real-time and post-processed images may be shown. When the myocardium is to be examined for perfusion, it is highly desirable that backscattered ultrasound data should be analyzed and compared at identical phases of the cardiac cycle. Preferably, although not necessarily, triggering occurs at diastole, when the heart is at rest. This triggering is accomplished by a triggering circuit 36 that is responsive to an electrocardiogram (EKG) waveform developed by suitable monitoring apparatus (not shown). When a particular point in the cardiac cycle is reached, for example when the R portion of the QRS wave in the EKG waveform is developed, the circuit 36 allows a full frame of scan line data to pass to the frequency analyzer 28. Alternatively, triggering (or capture of data) may occur at multiple points in the cardiac cycle, if desired. Such triggering is accomplished in conventional ultrasound machines and will be readily apparent to one of ordinary skill in the art.

The detected frequency characteristics may be analyzed in any of a number of different ways in order to obtain an indication of perfusion. For example, as shown in FIG. 3, the ratio A1/A2 of the first and second frequency component amplitudes may be obtained from the baseline reflection signal and compared with the ratio A3/A4 of the first and second frequency component amplitudes in the post-introduction reflection signal. If the difference between these ratios exceeds a reference level (set by a signal-to-noise ratio), the color coder develops a display signal that causes the display 18 to display a particular color at a corresponding point in the image with an intensity that varies with the amplitude of the ratio difference. Alternatively, the hue of the displayed color may be varied with the magnitude of the ratio difference.

As an alternative, the frequency analyzer 28 may detect a characteristic of the overall frequency spectra of the reflected signals, rather than a characteristic of one or more frequency components. In this embodiment, the width of the frequency spectrum of a reflected signal, the mean frequency, the skewness or kurtosis of the spectrum or the like may be detected in the absence and presence of contrast agent in the tissue and these frequency parameters may be compared by the comparator 32 and the results of the comparison passed to the color coder 34 for development of color display data. In this way, a spatial representation of the distribution of the microbubbles within the tissues visualized in the imaging scan plane may be obtained.

Figure 5:
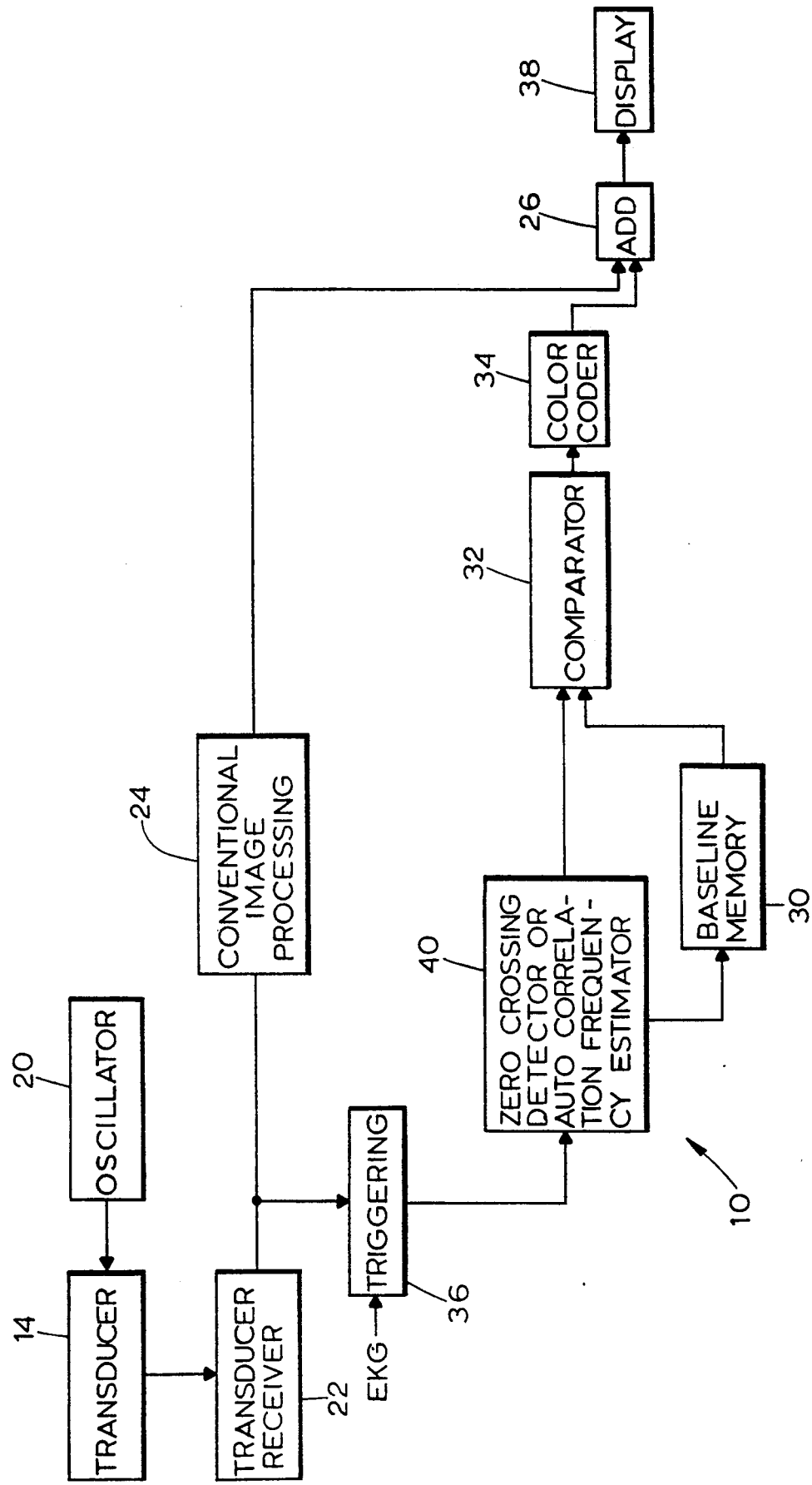

Referring now to FIG. 5, there is illustrated a further embodiment of the present invention. Elements common to FIGS. 4 and 5 are assigned the same reference numeral. In the system of FIG. 5, the frequency analyzer 28 (FIG. 4) is illustrated as comprising a zero crossing detector or an autocorrelation frequency estimator 40. Backscattered frequency information may be derived from multiple points over the image plane by utilizing a zero crossing detector that counts how many times the reflected signal passes through zero within a specific time period. The number of times the reflected signal passes through zero is roughly proportional to the frequency of the waveform over that time and space. While this conventional method of obtaining frequency information is rather crude, such an analysis can be undertaken rapidly and is therefore suitable for real time applications.

Alternatively, conventional autocorrelation techniques utilized in Doppler color flow mapping technology may be used to obtain the frequency information. Such techniques are disclosed in the following book, the disclosure of which is hereby incorporated by reference herein:

Color Atlas of Real-Time Two-Dimensional Echocardiography, pp. 7-36 (R. Omoto, ed.), Shindan-To-Chiro Co., Ltd., Tokyo (1984).

The remainder of the methodology is identical to that of FIG. 4.

Figure 6:
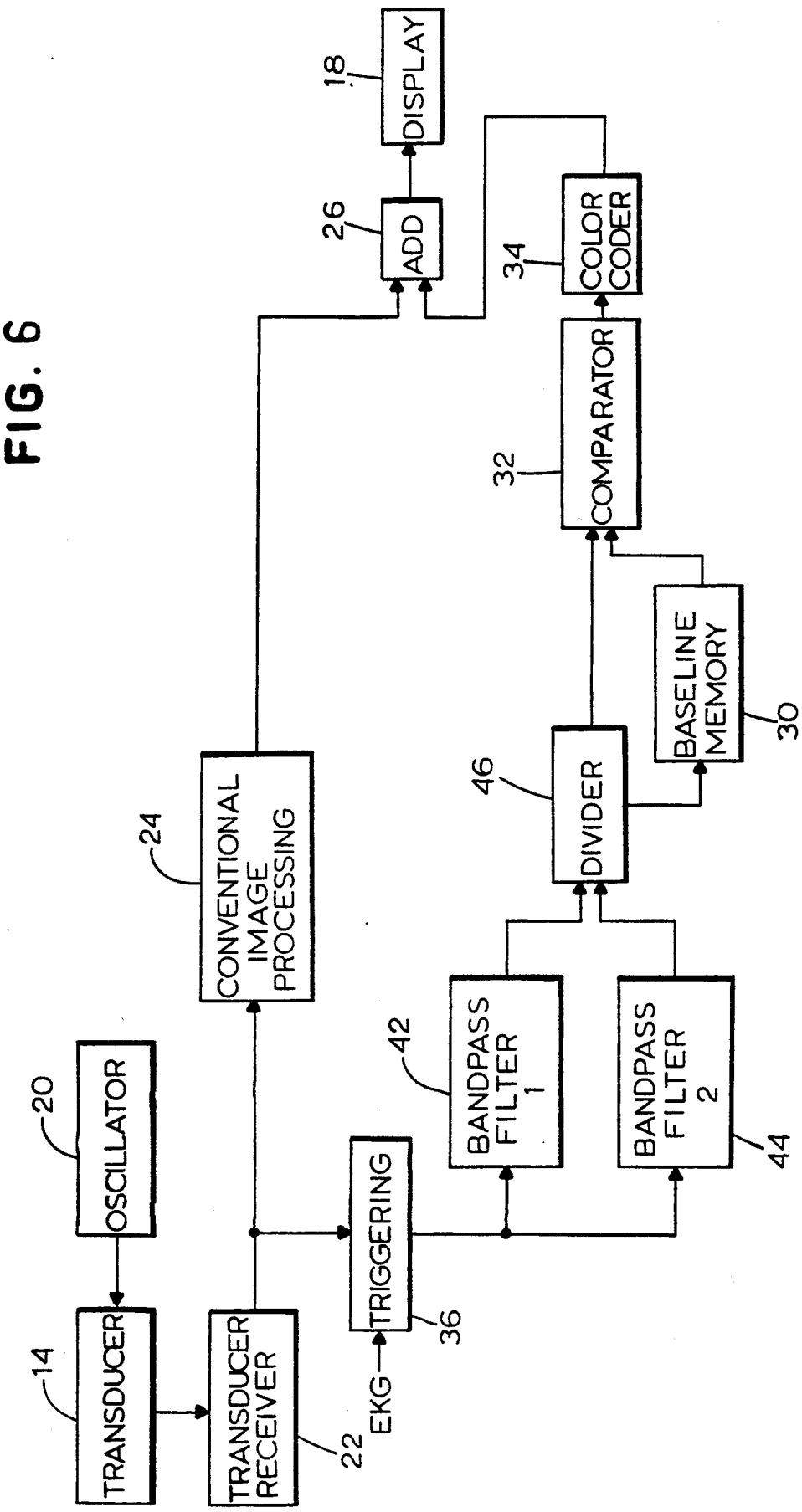

FIG. 6 illustrates a preferred form of the present invention. Again, elements common to FIGS. 4 and 6 are assigned like reference numerals. The frequency analyzer 28 of FIG. 4 is illustrated as comprising first and second narrow bandpass filters 42, 44 and a divider 46. One of the bandpass filters 42, 44 has a center frequency coincident with the in-vivo resonant frequency of the contrast microbubbles. The other bandpass filter has a center frequency removed from the center frequency of the first bandpass filter but within the transducer response frequency band. The amplitudes of the output signals of the bandpass filters 42, 44 are divided by the divider 46 both during baseline measurement (during which the result of the division is stored in the baseline memory 30) and after the introduction of contrast microbubbles into the tissue undergoing study. As before, the ratios are compared by the comparator 32 and the color coder 34 develops display information in accordance with the comparison which is combined by the combiner 26 with the conventional image data and provided to the display 18.

It should be noted that additional frequency selective filters might be used so that other frequencies are detected and analyzed. Because of the frequency dependent effect of the backscatter, the relationships of the signal amplitudes from the filters are changed by the introduction of contrast microbubbles into the tissues undergoing examination.

In addition, in an alternative embodiment, one or both of the filters 42 and 44 may be a variable bandpass filter that may be tuned or set to select a predetermined frequency to provide greater flexibility. For example, different contrast agents may have different resonant frequencies in tissue. Thus, one of the filters 42 and 44 may be tuned or set to pass reflected energy having a frequency corresponding to the resonant frequency in tissue of the selected contrast agent, and the other filter, for example, may be set or tuned to the center frequency of the transducer 14.

Figure 7:
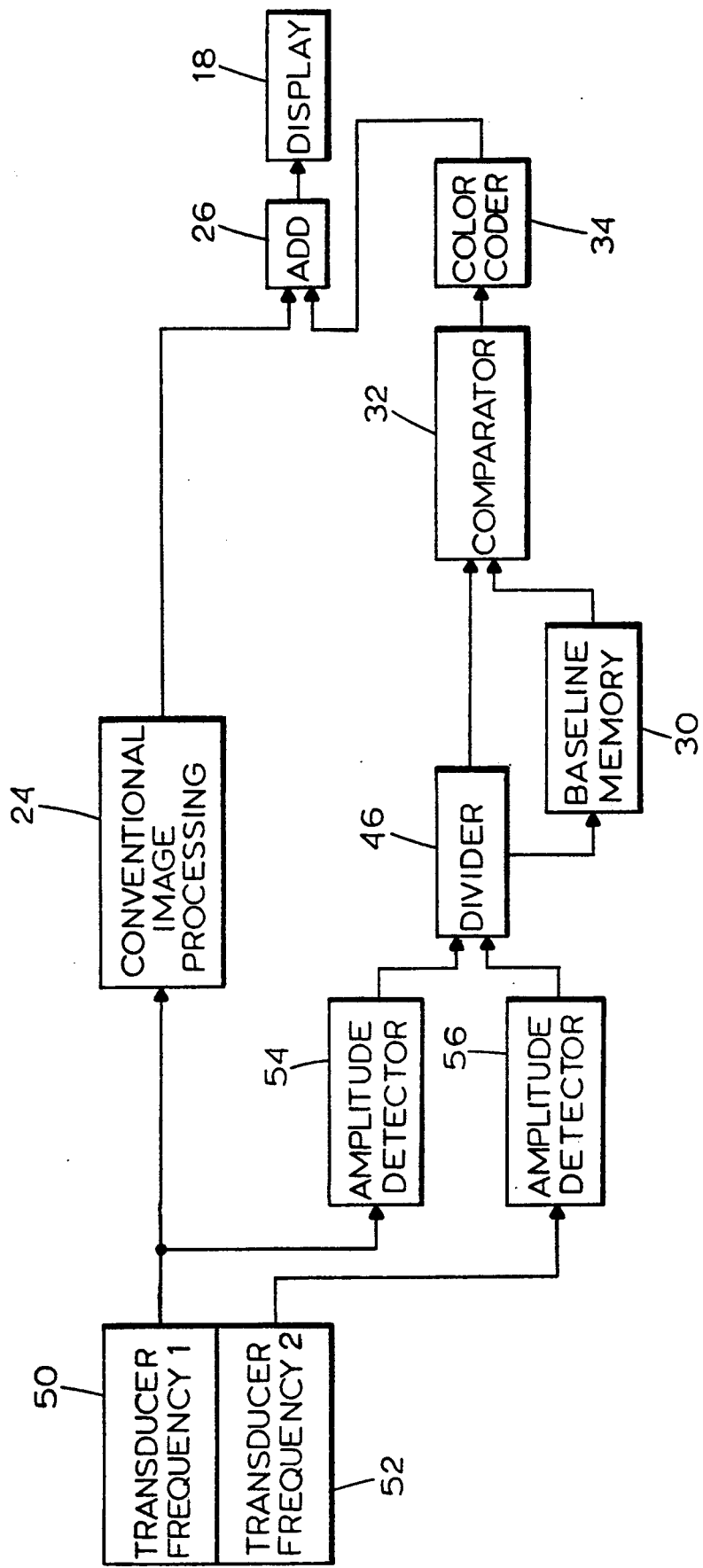

FIG. 7 illustrates yet another alternative embodiment. Here, the oscillator 20, transducer receiver circuit 22 and triggering circuitry 36 are not shown for purposes of simplicity. Further, the single transducer 14 is replaced by two transducers 50, 52. The second transducer 52 develops ultrasonic energy at a center frequency substantially coincident with the in-vivo resonant frequency of the contrast microbubbles. The first transducer 50 develops ultrasonic energy at a reference frequency other than the resonant frequency.

Alternatively, the two transducers may be replaced by a single transducer alternately driven at the reference and resonant frequencies.

The reflected signals developed by the transducers 50 and 52 are provided to first and second amplitude detectors 54, 56 that replace the frequency analyzer 28 of FIG. 4 and that detect the amplitudes of the reference and resonant frequency components in the baseline and post-introduction reflection signals, respectively. Alternatively, the frequency detector 56 may detect the amplitude of a harmonic of the resonant frequency. In addition, the reflection signal from the first transducer 50 is utilized by the conventional image processing circuit 24 to obtain the tissue display data.

The outputs of the amplitude detectors 54 and 56 are provided to the divider 46, which in turn obtains baseline and post-introduction ratios that are compared by the comparator 32 as before. Also as previously noted, the output of the comparator 32 is provided by the color coder 34 and the combiner 26 to the display 18. Sequential ultrasound pulses at the resonant and reference frequencies are transmitted down each scan line and the ratios of backscattered amplitudes from both frequency pulses are examined at multiple positions down the image scan lines. Because of the frequency dependent effect of the backscatter, the ratios of signal amplitudes from the different frequency pulses are modified by the introduction of contrast microbubbles within the tissues. The baseline ratio is determined in the absence of microbubbles in the tissues and then the magnitude of a shift in the ratio caused by introduction of contrast agent is determined at multiple points over the image to obtain an indication of microbubble distribution within the tissues.

The following books disclose ultrasonic examination systems and techniques and the use of microbubbles as a contrast agent and are expressly incorporated by reference herein:

Mark J. Monaghan, Practical Echocardiography And Doppler, John Wiley and Sons, (1990, reprinted July, 1991);

Harvey Feigenbaum, Echocardiography, Lea and Febiger, (1981); and

Digital Techniques in Echocardiography, (Jay Roelandt, ed.), Martinus Najhoff Publishers, (1987).

Numerous modifications and variations of the invention will be apparent to those skilled in the art in view of the foregoing description. Thus, it is to be understood that, within the scope of the appended claims, the invention may be practiced other than as specifically described hereinabove.

What is claimed and desired to be secured by Letters Patent is:

1. A method of ultrasonically measuring tissue perfusion using an ultrasound contrast enhancing agent, the method comprising the steps of:
    (a) insonating the tissue with ultrasonic energy during a first time period in the absence of the agent in the tissue and during a second time period in the presence of the agent in the tissue;
    (b) detecting a frequency characteristic of ultrasonic energy reflected by the tissue during the first time period to obtain baseline frequency data;
    (c) detecting the frequency characteristic of the ultrasonic energy reflected by the tissue during the second time period to obtain post-introduction frequency data; and
    (d) using the baseline frequency data and the post-introduction frequency data while the agent is present in the tissue to obtain a real-time indication of spatial distribution of the contrast agent in the tissue.

2. The method of claim 1, wherein the reflected ultrasonic energy includes first and second frequency components each of which has an amplitude and wherein each of the steps (b) and (c) comprises the step of detecting the amplitudes of the first and second frequency components.

3. The method of claim 2, wherein the step (d) comprises the steps of dividing the first frequency amplitude detected during the step (b) by the second frequency amplitude detected during the step (b) to derive a first ratio, dividing the first frequency amplitude detected during the step (c) by the second frequency amplitude detected during the step (c) to derive a second ratio and comparing the first and second ratios.

4. The method of claim 3, wherein the step (d) further includes the step of operating a display in real time in accordance with the comparison of the first and second ratios to obtain the indication of presence.

5. The method of claim 4, wherein the display is of the color type and further including the step of deriving image data from the reflected ultrasonic energy representing an image of the tissue and wherein the step of operating comprises the step of using a color coder to develop color display data based on the comparison of the first and second ratios, combining the image data with the color display data to obtain combined data and providing the combined data to the display.

6. The method of claim 3, wherein the step (a) comprises the step of operating a transducer to sequentially insonate the tissue with ultrasonic energy at a first frequency and at a second frequency spaced in the frequency spectrum from the first frequency and wherein each of the steps (b) and (c) further includes the step of using the transducer to develop a reflection signal representing the reflected ultrasonic energy.

7. The method of claim 6, wherein each of the steps (b) and (c) includes the step of sequentially applying the reflection signal to first and second amplitude detectors that detect the amplitudes of the first and second frequency components of the energy.

8. The method of claim 7, wherein the step (d) includes the step of operating a color display in accordance with the comparison of the first and second ratios.

9. The method of claim 2, wherein the step (a) comprises the step of operating a transducer to insonate the tissue and wherein each of the steps (b) and (c) further includes the step of using the transducer to develop a reflection signal representing the reflected ultrasonic energy.

10. The method of claim 9, wherein each of the steps (b) and (c) further includes the steps of providing the reflection signal to first and second bandpass filters having center frequencies substantially equal to the first and second frequencies to obtain first and second filtered signals and providing the first and second filtered signals to a divider to obtain divider a signal.

11. The method of claim 10, wherein the step (b) further includes the step of providing a memory for storing the baseline frequency data.

12. The method of claim 9, wherein each of the steps (b) and (c) includes the step of using a frequency analyzer to analyze the reflection signal and to develop the baseline frequency data and the post-introduction data, wherein the step (b) includes the step of storing the baseline frequency data in a memory and wherein the step (d) includes the step of comparing the stored baseline frequency data with the post-introduction data.

13. The method of claim 12, wherein the step of using the frequency analyzer includes the step of processing the reflection signal in accordance with a Fast Fourier transformation algorithm.

14. The method of claim 12, wherein the step of using the frequency analyzer includes the step of processing the reflection signal in accordance with a Chirp-Z algorithm.

15. The method of claim 12, wherein the frequency analyzer comprises a zero crossing detector.

16. The method of claim 12, wherein the frequency analyzer comprises an autocorrelation frequency estimator.

17. The method of claim 1, wherein the step (a) comprises the step of sequentially directing the ultrasonic energy along scan lines and including the further step of repeating the steps (b) and (c) a plurality of times for each scan line.

18. A system for detecting tissue perfusion using a contrast agent, comprising:
    a transducer capable of directing ultrasonic energy at first and second different frequencies toward tissue wherein the contrast agent has a resonant frequency in the tissue and the first frequency is substantially equal to the resonant frequency, the transducer also being capable of developing a baseline reflection signal and a post-introduction reflection signal representative of ultrasonic energy reflected by the tissue prior to and after introduction of the contrast agent into the tissue, respectively;

means coupled to the transducer for detecting a frequency characteristic of the baseline reflection signal and frequency characteristic of the post-introduction reflection signal; and means operable when the contrast agent is in the tissue for developing a real-time indication of tissue perfusion from the detected frequency characteristic of the baseline reflection signal and the detected frequency characteristic of the post-introduction reflection signal.

19. The system of claim 18, wherein the detecting means further includes means for storing the frequency characteristic of the baseline reflection signal and means for comparing the frequency characteristic of the post-characteristic of the baseline reflection signal.

20. The system of claim 19, wherein the developing means includes a color coder coupled to the comparing means and a display coupled to the color coder.

21. The system of claim 20, further including means coupled to the transducer for deriving image data representing an image of the tissue and wherein the developing means further includes means for combining the image data with color data developed by the color coder to obtain data for the display.

22. The system of claim 18, wherein the detecting means comprises first and second bandpass filters having first and second center frequencies, respectively, a divider coupled to the first and second bandpass filters wherein the divider calculates a baseline amplitude ratio and a post-introduction amplitude ratio and a comparator for comparing the baseline and post-introduction amplitude ratios.

23. The system of claim 18, wherein the detecting means comprises a frequency analyzer that analyzes the baseline reflection signal and the post-introduction reflection signal.

24. The system of claim 23, wherein the frequency analyzer implements a Fast Fourier transformation algorithm.

25. The system of claim 23, wherein the frequency analyzer implements a Chirp-Z algorithm.

26. The system of claim 23, wherein the frequency analyzer comprises a zero crossing detector.

27. The system of claim 23, wherein the frequency analyzer comprises an autocorrelation frequency estimator.

28. The system of claim 18, wherein the transducer is operated to sequentially direct ultrasonic pulses at the first and second frequencies along a scan line and wherein the detecting means comprises a first amplitude detector for detecting a frequency component amplitude at the first frequency and a second amplitude detector for detecting a frequency component amplitude at the second frequency.

29. The system of claim 18, wherein the transducer is operated to sequentially direct ultrasonic pulses at the first and second frequencies along a scan line and wherein the detecting means comprises a first amplitude detector for detecting a frequency component amplitude at a harmonic of the first frequency and a second amplitude detector for detecting a frequency component amplitude at the second frequency.

30. A system for ultrasonically examining blood flow through at a part of a living body using a contrast agent injectable into the flow of blood through the part, comprising:

means for insonating the part with ultrasonic energy at first and second frequencies during a first time period when the contrast agent is present in the part and during a second time period when contrast agent is not in the part;

means operable a plurality of times during each of the first and second time periods for detecting amplitudes of first and second frequency components of the ultrasonic energy reflected from the part during the first and second time periods;

means coupled to the detecting means for comparing the amplitudes detected during the first time period with the amplitudes detected during the second time period; and means coupled to the comparing means for operating a display in accordance with the comparison to obtain an indication of blood flow.

31. The system of claim 30, wherein the detecting means comprises first and second bandpass filters having center frequencies at the first and second frequencies, respectively, and a divider having inputs coupled to the first and second bandpass filters and an output coupled to the comparing means wherein the divider calculates first and second amplitude ratios and the comparing means compares the first and second amplitude ratios.

32. The system of claim 31, further including means coupled between the divider and the comparing means for storing the first amplitude ratio wherein the comparing means compares the stored first amplitude ratio with the second amplitude ratio.

33. The system of claim 32, wherein the operating means comprises a color coder coupled between the comparing means and the display.

34. The system of claim 33, further including means coupled to the insonating means for deriving image data representing the part and wherein the operating means further includes means for combining the image data with color data developed by the color coder to obtain data for the display.

35. The system of claim 30, wherein the detecting means comprises a frequency analyzer that implements a Fast Fourier transformation algorithm.

36. The system of claim 30, wherein the detecting means comprises a frequency analyzer that implements a Chirp-Z algorithm.

37. The system of claim 30, wherein the insonating means comprises a transducer operated to sequentially direct ultrasonic pulses at the first and second frequencies along a scan line and wherein the detecting means comprises first and second amplitude detectors.

38. A system for ultrasonically examining blood flow through at least a part of a living body, comprising:

means for directing incident ultrasonic energy over a first frequency spectrum to the part wherein reflected ultrasonic energy is reflected by the part over a second frequency spectrum;

means for sensing the reflected ultrasonic energy from the part;

means coupled to the sensing means for detecting a frequency characteristic of the second frequency spectrum under nonenhanced and enhanced contrast conditions;

means coupled to the detecting means for comparing the frequency characteristic detected under the nonenhanced contrast condition with the frequency characteristic detected under the enhanced contrast condition;

a color display; and means coupled to the comparing means for operating the display in accordance with the comparison undertaken by the comparing means, thereby to provide a color-coded visual image of the part and the blood flow therethrough.

39. The system of claim 38, wherein the second frequency spectrum includes first and second frequency components each having a magnitude and wherein the detecting means includes means for developing first and second signals representing the magnitudes of the first and second frequency components, respectively.

40. The system of claim 39, wherein the detecting means further includes a divider for dividing the first and second signals under the nonenhanced and enhanced conditions to obtain nonenhanced and enhanced ratios, respectively, wherein the nonenhanced and enhanced ratios are compared by the comparing means.

41. The system of claim 40, wherein the developing means comprises first and second bandpass filters having center frequencies at the first and second frequencies.

42. A method of ultrasonically examining tissue using an ultrasound contrast enhancing agent, the method comprising the steps of:

(a) insonating the tissue with ultrasonic energy including first and second frequency components, each of which has an amplitude during a first time period in the absence of the agent in the tissue and during a second time period in the presence of the agent in the tissue;

(b) detecting the amplitudes of the first and second frequency components in the ultrasonic energy reflected by the tissue during the first time period to obtain baseline frequency data;

(c) detecting the amplitudes of the first and second frequency components in the ultrasonic energy reflected by the tissue during the second time period to obtain post-introduction frequency data; and (d) using the baseline frequency data and the post-introduction frequency data to obtain an indication of presence of the agent in the tissue.

43. The method of claim 42, wherein the step (d) comprises the steps of dividing the first frequency amplitude detected during the step (b) by the second frequency amplitude detected during the step (b) to derive a first ratio, dividing the first frequency amplitude detected during the step (c) by the second frequency amplitude detected during the step (c) to derive a second ratio and comparing the first and second ratios.

44. The method of claim 43, wherein the step (d) further includes the step of operating a display in real-time in accordance with the comparison of the first and second ratios to obtain the indication of presence.

45. The method of claim 44, wherein the display is of the color type and further including the step of deriving image data from the reflected ultraonic energy representing an image of the tissue and wherein the step of operating comprises the step of using a color coder to develop color display data based on the comparison of the first and second rations, combining the image data with the color display data to obtain combined data and providing the combined data to the display.

46. The method of claim 42, wherein the step (a) comprises the step of sequentially insonating the tissue at the first and second frequencies and wherein each of the steps (b) and (c) further includes the step of developing a reflection signal representing the reflected ultrasonic energy.

47. The method of claim 46, wherein each of the steps (b) and (c) further includes the step of providing the reflection signal to first and second bandpass filters having center frequencies substantially equal to the first and second frequencies to obtain first and second filtered signals and wherein the step (d) includes the step of providing the first and second filtered signals to the divider to obtain a divider signal.

48. The method of claim 47, wherein the step (d) further includes the step of providing a memory for storing the baseline frequency data.

* * * * *